(12) United States Patent
Schweke et al.

(10) Patent No.: US 10,487,252 B2
(45) Date of Patent: Nov. 26, 2019

(54) WATER BASED THERMAL COOLING GELS COMPRISING A VISCOSITY MODIFIER AND ICE NUCLEATING PROTEIN

(71) Applicant: Microtek Laboratories, INC., Dayton, OH (US)

(72) Inventors: Madison B Schweke, Union, OH (US); Jessica P Davis, Kettering, OH (US); Carl M Lentz, Waynesville, OH (US)

(73) Assignee: Microtek Laboratories, INC., Dayton, OH (US)

( * ) Notice: Subject to any disclaimer, the term of this patent is extended or adjusted under 35 U.S.C. 154(b) by 0 days.

(21) Appl. No.: 16/255,260

(22) Filed: Jan. 23, 2019

(65) Prior Publication Data

US 2019/0225853 A1 Jul. 25, 2019

Related U.S. Application Data

(60) Provisional application No. 62/621,322, filed on Jan. 24, 2018.

(51) Int. Cl.
*C09K 5/06* (2006.01)
*F28D 20/02* (2006.01)

(52) U.S. Cl.
CPC .............. *C09K 5/066* (2013.01); *F28D 20/02* (2013.01)

(58) Field of Classification Search
CPC ................................ C09K 5/066; F28D 20/02
USPC .......................................................... 252/73
See application file for complete search history.

(56) References Cited

U.S. PATENT DOCUMENTS

| | | |
|---|---|---|
| 3,780,537 A | 12/1973 | Spencer |
| 3,950,158 A | 4/1976 | Gossett |
| 3,977,202 A | 8/1976 | Forusz et al. |
| 4,081,256 A | 3/1978 | Donnelly |
| 5,065,758 A | 11/1991 | Whitehead et al. |
| 5,181,394 A | 1/1993 | Schea, III et al. |
| 5,352,502 A | 10/1994 | Fuller |
| 5,478,988 A | 12/1995 | Hughes et al. |
| 6,099,555 A | 8/2000 | Sabin |
| 6,233,945 B1 | 5/2001 | Kohout |
| 6,610,084 B1 | 8/2003 | Torres |
| 8,122,844 B2 * | 2/2012 | Smith ................... G01K 11/08 116/216 |
| 8,671,871 B2 * | 3/2014 | Huffman ............... G01K 3/04 116/207 |
| 10,125,297 B2 * | 11/2018 | Lentz ..................... C09K 5/063 |
| 2004/0109853 A1 * | 6/2004 | McDaniel ............... A62D 3/02 424/94.6 |
| 2005/0175665 A1 * | 8/2005 | Hunter ................... A61K 45/06 424/423 |
| 2006/0137389 A1 | 6/2006 | Shah et al. |
| 2010/0210745 A1 * | 8/2010 | McDaniel .............. C09D 5/008 521/55 |
| 2010/0312045 A1 * | 12/2010 | Ramlov ................... A01N 1/02 600/35 |
| 2011/0033391 A1 * | 2/2011 | Weiner ................... A21D 8/042 424/48 |
| 2013/0004936 A1 * | 1/2013 | Fujikawa .............. C07D 311/62 435/1.3 |
| 2013/0011884 A1 | 1/2013 | Ichihara et al. |
| 2013/0196044 A1 | 8/2013 | Winston et al. |
| 2014/0150464 A1 | 6/2014 | Bloedow et al. |
| 2015/0313950 A1 * | 11/2015 | Gammelsaeter ..... A61K 35/655 424/523 |
| 2017/0029476 A1 * | 2/2017 | De Jong ................ C07K 14/39 |
| 2017/0326042 A1 | 11/2017 | Zeng et al. |
| 2018/0160695 A1 * | 6/2018 | Dekker .............. A23C 19/0684 |
| 2018/0242665 A1 * | 8/2018 | Ryan ..................... A41D 31/02 |

FOREIGN PATENT DOCUMENTS

| | | |
|---|---|---|
| JP | H10204424 | 8/1998 |
| WO | 2016166548 A1 | 10/2016 |

OTHER PUBLICATIONS

Michiko Watanabe, Jun Watanabe, Keiko Kumeno, Nobuko Nakahama & Soichi Arai (1989) Freeze Concentration of Some Foodstuffs Using Ice Nucleation-active Bacterial Cells Entrapped in Calcium Alginate Gel, Agricultural and Biological Chemistry, 53:10, 2731-2735.
Soichi Arai & Michiko Watanabe (1986) Freeze Texturing of Food Materials by Ice-nucleation with the Bacterium Erwinia ananas, Agricultural and Biological Chemistry, 50:1, 169-175.
PCT, International Search Report; International Application No. PCT/US2019/014752 (dated Apr. 11, 2019) (2 pages).
PCT, International Search Report Written Opinion, International Application No. PCT/US2019/014752 (dated Apr. 11, 2019) (1 page).

* cited by examiner

*Primary Examiner* — Douglas J McGinty
(74) *Attorney, Agent, or Firm* — FisherBroyles, LLP; Susan M. Oiler

(57) ABSTRACT

Thermal cooling gel and cold packs enclosing such thermal cooling gel have an aqueous gel of 1% to 10% wt/wt of cellulose, 0.5 g/L to 2 g/L of an ice nucleating protein, and a biocide. The enthalpy of the thermal cooling gel is in a range of 250 J/g to 330 J/g.

22 Claims, 4 Drawing Sheets

WATER BASED THERMAL COOLING GELS COMPRISING A VISCOSITY MODIFIER AND ICE NUCLEATING PROTEIN

TECHNICAL FIELD

The present application relates to a water based thermal cooling gel for use cooling products in the food and beverage industry, cooling pharmaceuticals and biotech products, as a cold compress, and other applications, more particularly, to a thermal cooling gel that has an ice nucleating protein and a thickness tailored for the end use by the concentration of a viscosity modifier.

BACKGROUND

Phase change materials (PCMs) have been utilized as thermal energy storage systems for decades due to their ability to store and release energy in the form of heat during a phase transition, most commonly from the solid to liquid states. PCMs exist in many forms including organic, inorganic, eutectics, and solid-solid. With this wide variety, a range of temperatures for different applications can be achieved. It is important to have a PCM temperature in a workable range for the application in order to get the full charge of energy out of the system. These storage systems can be implemented in many different applications such as bedding, textiles, electronics, bio-tech, and pharmaceutical.

A commonly known application of energy storage is in the form of cold pack therapy. Cold packs are generally water based formulations that once active, keep their surroundings cold for a specified amount of time. They are commonly used as first aid relief, and food and beverage controlled refrigeration. Water is one of the best known PCMs due to its high latent heat value of 332 J/g, but water also has disadvantages. Water melts around 0° C., however, it can be super cooled to temperatures on the order of −40° C. Most commercial freezers only reach temperatures in the −23° C. to −15° C. range, which presents a problem for a water based formulation that requires freeze temps lower than that to charge the PCM completely.

While there are commercial products, such as instant ice packs, that base their phase change on the presence of water, its efficacy is often diluted by the other additives needed to improve the formula in other areas, like viscosity, and freeze temperature. Often times these additives dilute the enthalpy available of the water, therefore hindering its efficacy as a PCM.

There is a need for new and improved cold packs or other thermal cooling products that corrects the fundamental issues of using water as the PCM, noted above, in such products.

SUMMARY

Longer performing ice packs having a thermal cooling gel are disclosed that maintain a temperature of 5° C. for more than twice as long as commercially available ice packs and that refreeze at least 45 minutes faster. The thermal cooling gel is an aqueous gel comprising 1% to 10% wt/wt of cellulose, 0.5 g/L to 2 g/L of an ice nucleating protein, and a biocide, and the enthalpy of the thermal cooling gel is in a range of 250 J/g to 330 J/g.

In all aspects, the cellulose is selected from the group comprising sodium carboxymethylcellulose, hydroxypropyl cellulose, methylcellulose, methyl hydroxyethyl cellulose, methyl hydroxypropyl cellulose, hydroxyethyl cellulose, carboxymethyl methylcellulose, cellulose ethers, mixed cellulose ethers, and combinations thereof. In one embodiment, the cellulose comprises methylcellulose. In another embodiment, the cellulose comprises methyl cellulose and methyl hydroxyethyl cellulose. In another embodiment, the cellulose comprises methyl cellulose, methyl hydroxyethyl cellulose, and methyl hydroxypropyl cellulose.

In all aspects, the ice nucleating protein is selected from the group consisting of pseudomonas syringae, pseudomonas fluorescens, Erwinaia herbicola, and combinations thereof and is 0.001% to 1% wt/wt of the aqueous gel. In one embodiment, the biocide is selected from the group consisting of silver nanoparticles, an herb extract of thyme, and combinations thereof.

In one aspect, the aqueous gel has 1% to 5% wt/wt cellulose, an enthalpy in a range of 300 J/g to 330 J/g, and a viscosity of 25 cps to 7,000 cps.

In one aspect, the aqueous gel has 5% to 10% wt/wt cellulose, an enthalpy in a range of 250 J/g to 300 J/g, and a viscosity of 7,000 cps to 65,000 cps.

In another aspect, cold packs are disclosed that have a container with any of the thermal cooling gels disclosed herein enclosed within the container. The container may be a rigid container of a preselected shape and configuration or a flexible container that is conformable to a surface against which the flexible container is placed or seated. In all aspects, the container can permanently enclose the selected thermal cooling gel.

DETAILED DESCRIPTION

The following detailed description will illustrate the general principles of the invention, examples of which are additionally illustrated in the working and comparative examples.

Thermal cooling gels, which are a food grade formulation, are an aqueous gel comprising cellulose, an ice nucleating protein, and a biocide. The addition of the ice nucleating protein (INP) demonstrates the ability of the aqueous gel to freeze faster and maintain a lower temperature longer than without its usage. INPs work by inducing the formation of ice at warmer temperatures, generally around −5° C., whereas water without nucleation can be supercooled to temperatures on the order of −40° C. and below. The thermal cooling gel can be recharged or reused, freezes faster, and cools its environment longer than previous ice packs.

As used herein, "gel" means a coherent mass consisting of a liquid in which particles too small to be seen in an ordinary optical microscope are either dispersed or arranged in a fine network throughout the mass. A gel may be notably elastic and jellylike (as gelatin or fruit jelly), or quite solid and rigid (as silica gel, a material that looks like coarse white sand and is used as a dehumidifier). Gels are colloids (aggregates of fine particles, as described above, dispersed in a continuous medium) in which the liquid medium has become viscous enough to behave more or less as a solid.

The thermal cooling gel is an aqueous gel comprising 1% to 10% wt/wt of cellulose, 0.5 g to 2 g per liter of the aqueous gel is an ice nucleating protein, and a biocide. The enthalpy of the thermal cooling gel is in the range of 250 J/g to 330 J/g. The cellulose is selected from the group comprising sodium carboxymethylcellulose (CMC), hydroxypropyl cellulose (HPC), methylcellulose (MC), methyl hydroxyethyl cellulose (MHEC), methyl hydroxypropyl cellulose (MHPC), hydroxyethyl cellulose (HEC), carboxymethyl methylcellulose (CMMC), cellulose ethers, mixed cellulose ethers, and combinations thereof. In one embodiment, the cellulose comprises methylcellulose, or methyl cellulose and methyl hydroxyethyl cellulose, or methyl cellulose, methyl hydroxyethyl cellulose, and methyl hydroxypropyl cellulose. The concentration of the cellulose can negatively impact the freeing point and the enthalpy of the water, so a concentration within the range of 1% to 10% is preferred. If the thermal cooling gel is going to be housed in a rigid container (such as a hard-plastic container having a retained shape and form) then the concentration of the cellulose may be lower, e.g., 1% to 4%, which provides a less viscous gel. If the thermal cooling gel is going to be in flexible container (such as a plastic bag conformable to a surface, e.g., a person's neck), then the concentration of the cellulose may be higher, e.g., between 6% to 10%, which provides a more viscous gel.

Figure 1:
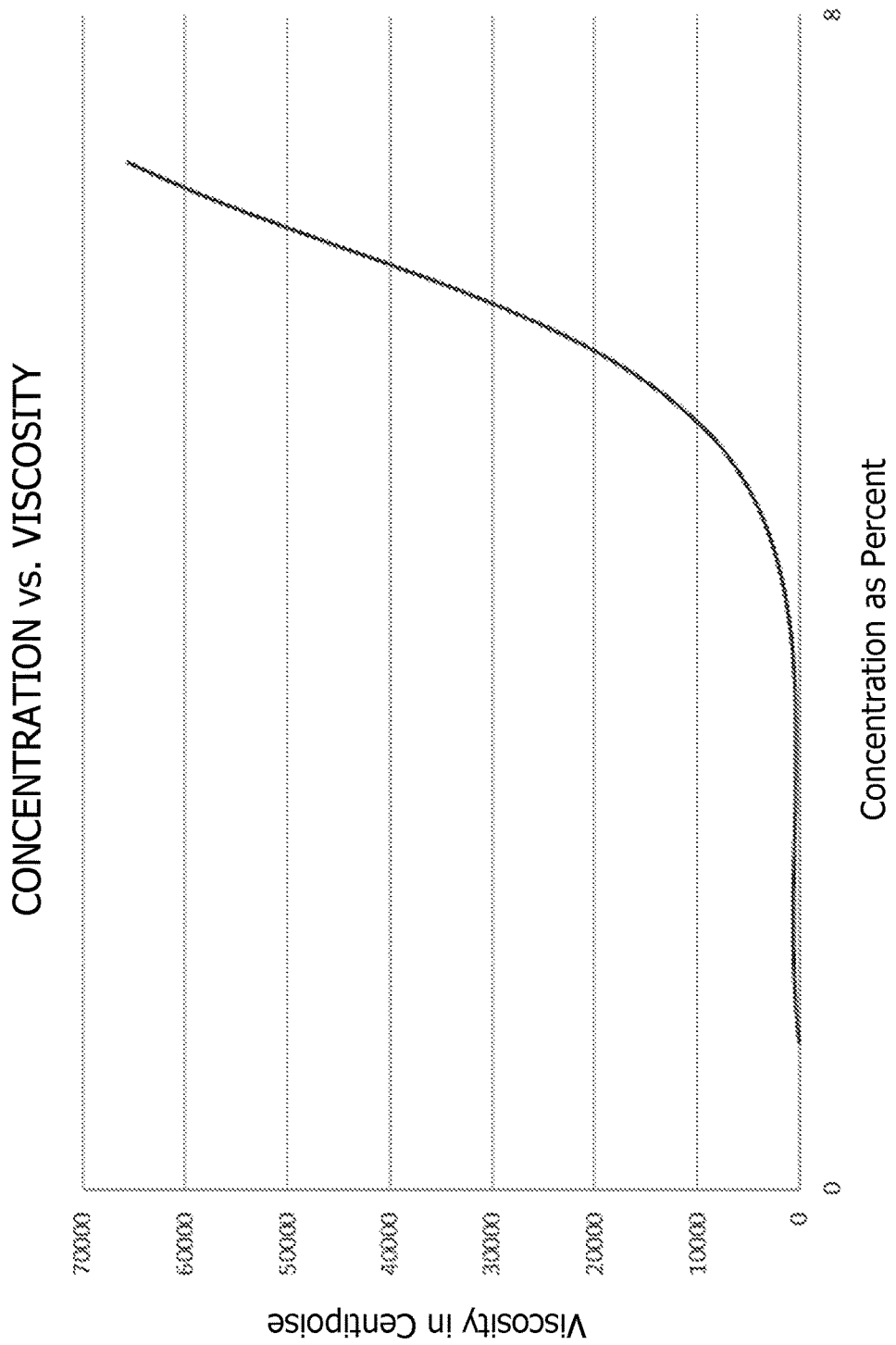
FIG. 1 is a graph of the change in viscosity of an aqueous gel as the concentration of cellulose is increased.
Figure 2:
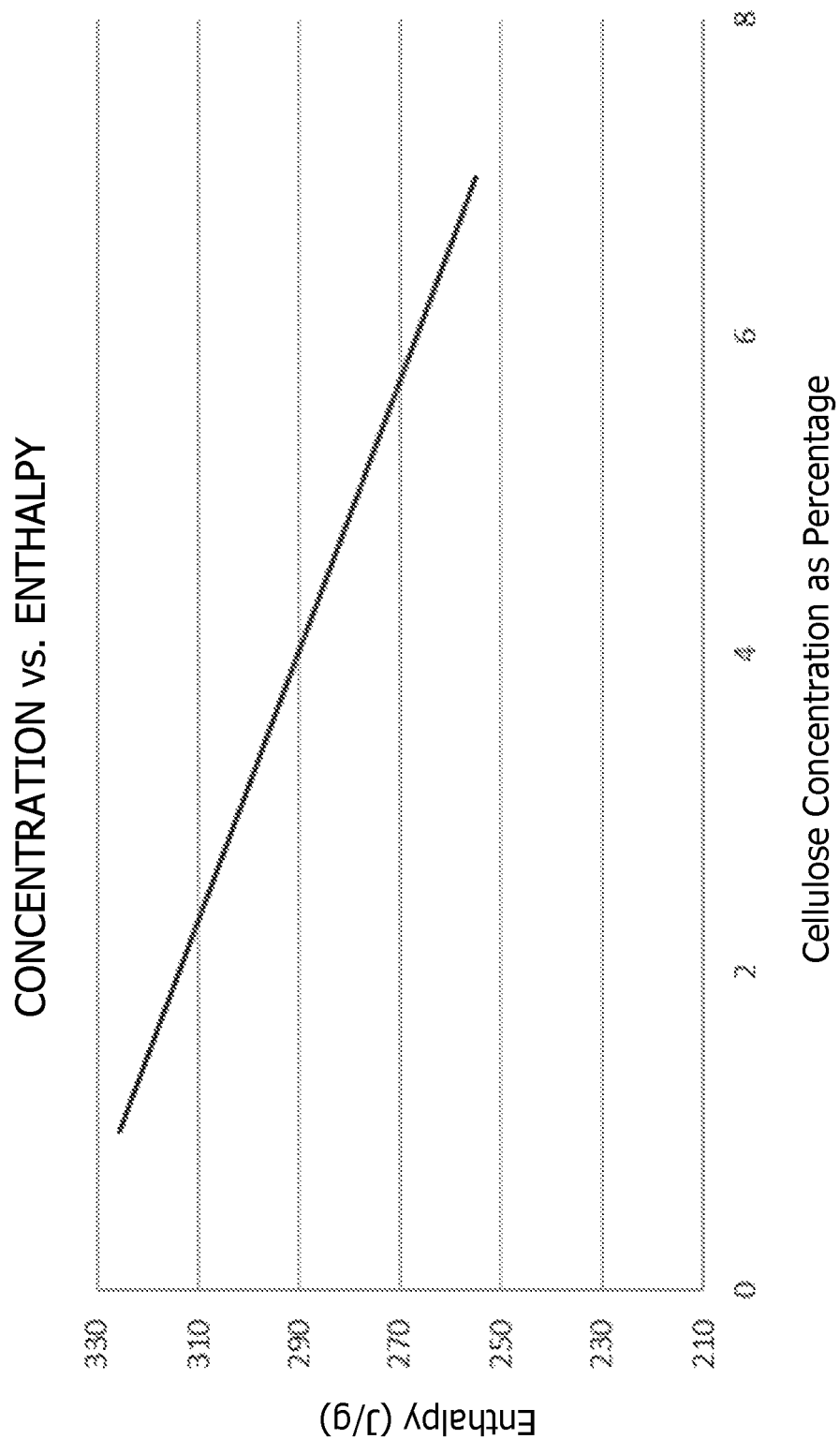
FIG. 2 is a graph of the change in the enthalpy of an aqueous gel as the concentration of cellulose is increased.
Figure 3:
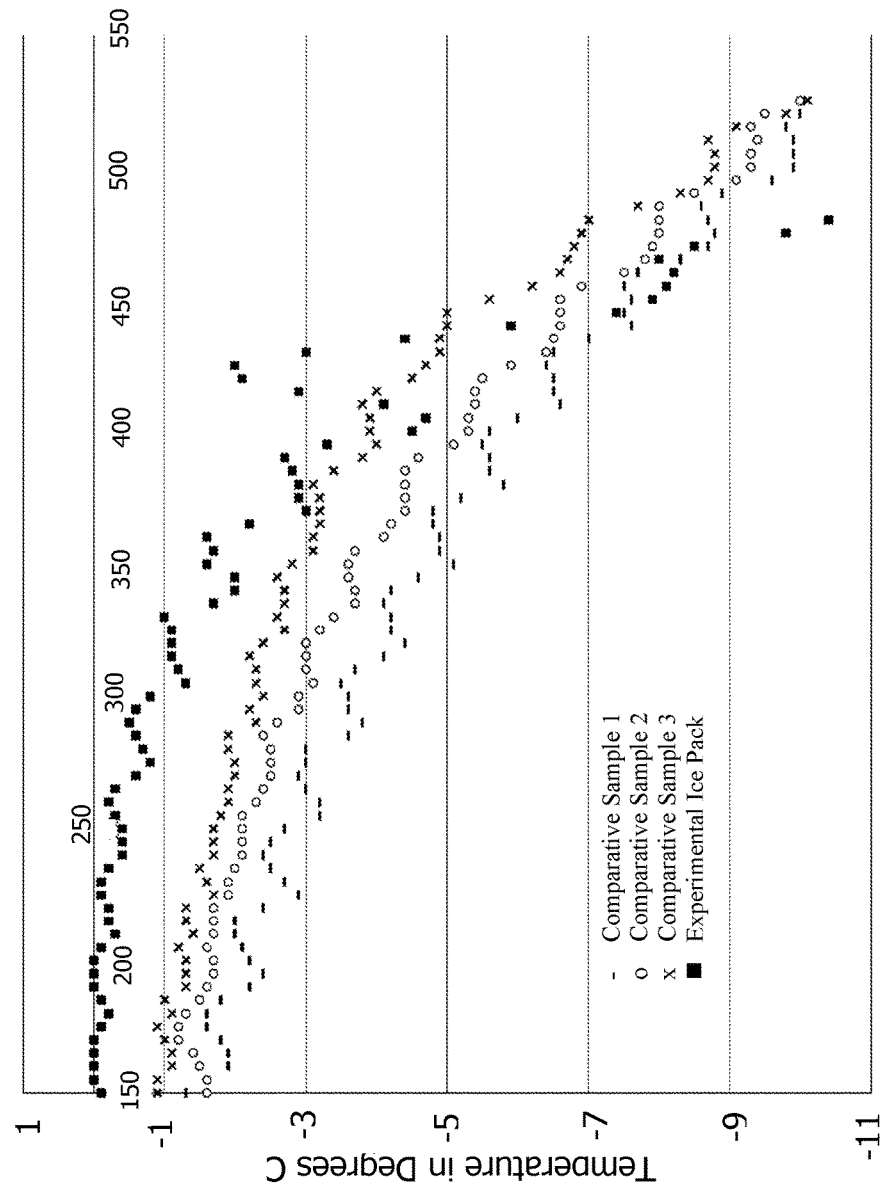
FIG. 3 is a graph of freeze data (time vs. temperature) for comparative samples and an experimental cooling gel.
Figure 4:
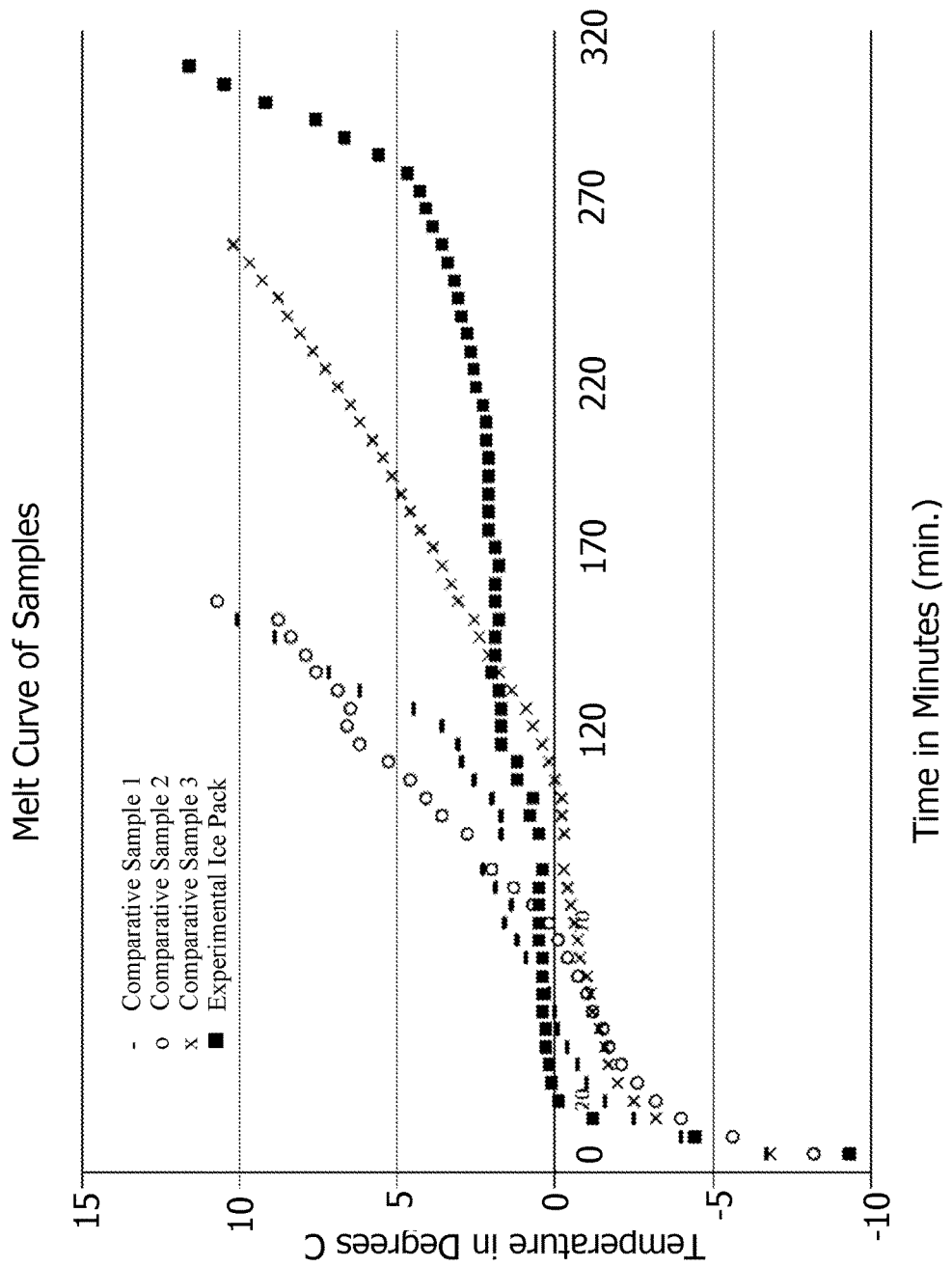
FIG. 4 is a graph of melt data (time vs. temperature) for comparative samples and an experimental cooling gel.

Referring to FIG. 1, a graph of the concentration of the cellulose in water to the viscosity of the gel formed is shown. The viscosities range from 5,000 centipoise (cps) to 110,000 centipoise over the % weight/weight concentration of the cellulose of 1% to 10%. Referring to FIG. 2, a graph of the concentration of the cellulose in water to the enthalpy of the gel is shown. As represented by FIGS. 1 and 2, an aqueous gel having 1% to 5% wt/wt cellulose has an enthalpy in a range of 300 J/g to 330 J/g and a viscosity of 25 to 7,000 cps. An aqueous gel having 5% to 10% wt/wt cellulose has an enthalpy in a range of 250 J/g to 300 J/g and a viscosity of 7,000 to 65,000 cps. The ability to change the viscosity of the aqueous gel, while still maintaining a viable PCM (high enthalpy) is extremely helpful with the end use of the product. It allows the market to dictate the parameters and characteristics of the product, instead of the other way around.

The ice nucleating protein is selected from the group consisting of pseudomonas syringae, pseudomonas fluorescens, Erwinaia herbicola, and combinations thereof. A concentration range of 0.5 g to 2 g per liter of an individual ice nucleating protein can be combined with the aqueous gel to enhance its phase change abilities. Each ice nucleating protein would provide a different total change to the freeze point of the water, i.e., the aqueous gel. Increasing the freeze point of the water allows it to freeze quicker, which means the thermal cooling gel or a cool pack containing the same can be used more frequently. Pseudomonas syringae, for example, has been found to increase the freezing point by almost 20° C. depending on the concentration and method of introduction to the gel.

Due to the nature of cellulose, a biocide is recommended to combat bacterial and/or mold growth. The biocide is 0.001% to 1% wt/wt of the aqueous gel. Biocides tested and shown to be compatible with the aqueous gel (there is no change to the efficacy of the thermal cooling gel) are ionic silver, silver zeolite, silver nanoparticles in solution, and an herb extract of thyme. Other food and/or cosmetic grade biocides are suitable as well, including, but not limited to, alcohols (ethanol, 2-propanol, 2-phenoxyethanol), aldehydes (glutaraldehyde, formaldehyde, glyoxal), amines (diethylamine, glucoprotamin), isothiazolinones (chlormethylisothiazolinone/methylisothiazolinone), organic acids and esters (parabens, propionic acid, formic acid, benzoic acid, salicylic acid), and quarternary ammonium compounds (benzalkonium chloride, didecyldimethylammoniumchoride). The biocide can be selected depending on the system requirements and price point of the final product. The silver nanoparticles show effectiveness as low as 0.001% wt/wt, and the thyme extract is effective in the range of 0.1% and 1% wt/wt.

Advantages

The thermal cooling gels disclosed herein provide better control and longer lasting effect by changing the freeze temperature, such that the gel freezes quicker (in a shorter amount of time, which equates to a faster reset), and stays cold longer (the solid to liquid transition takes a longer amount of time). The INPs and the cellulose achieve this without detracting from the phase change effects of water, i.e., keeping the enthalpy as high as possible for the desired viscosity of the end product. This is a two-fold improvement over prior products, and the cold packs are reusable by simply refreezing.

Moreover, the thermal cooling gels use water, which has great energy storage capabilities because of its high latent heat value, it is low cost, nontoxic, non-flammable, and environmentally friendly. The cellulose concentration enables control of the viscosity, which provides manufacturing flexibility in selection of shape and construction for a container to house the gel, selection of a flexible container versus a rigid container. Also, the thermal cooling gels are food safe (food grade).

The gels disclosed herein can be housed in a container to form a cold pack. The container may be designed to permanently enclosed the thermal cooling gel therein. The container can be a rigid container that retains a preselected shape and configuration, or a flexible container that is conformable to surface against which the flexible container is seated. A rigid container may be made of glass, metal, hard-plastic or other suitable materials. A flexible container may be made of polymer films, plastics (such as a plastic in the form of a bag), watertight fabrics, or other suitable materials.

Example 1

A gel was formulated to be 7% wt/wt of a cellulose mixture of MC, MHEC, and MHPC, Culminal™ 500 methylcellulose derivatives available from Ashland Specialty Ingredients. The gel was made by weighing 250 grams of deionized water into a plastic container, which was placed on ice with overhead mixing at 100 rpm. The temperature of the water was monitored until at least 10° C. was reached, then 0.25 grams of milled pseudomonas syringae (milled via mortar and pestle), available as Snomax snow inducer from Snomax International, was added and allowed to stir briefly. Secondly, 18.8 grams of the Culminal™ 500 was added slowly to the mixture, increasing the speed to between 200-250 rpm. The mixture was allowed to stir until all components were in solution and a gel like material was formed.

A biocide may be added to the gel subsequent to the above steps, for example thymol was added in an amount within a range of 0.1% and 1% wt/wt. For the below biocide effectiveness test, thymol was present as 0.1% wt/wt of the cooling gel.

TABLE 1

| Week | 1 | 2 | 3 | 4 | 5 | 9 | 13 | 18 | 22 | 26 |
|---|---|---|---|---|---|---|---|---|---|---|
| Control 1% wt/wt cellulose | Growth | — | — | — | — | — | — | — | — | — |
| Control 5% wt/wt cellulose | Growth | — | — | — | — | — | — | — | — | — |
| Thymol | No | No | No | No | No | No | No | No | No | No |

The control samples at both 1% and 5% wt/wt cellulose grew bacteria within the first week of testing. The Experimental cooling gel with thymol showed no growth for a full eight months, at which time the testing was discarded since there was no indication of bacteria growth.

COMPARATIVE EXAMPLES

A thermal cooling gel (EXP. 1) was made according to the process in Example 1 above to have 1% wt/wt cellulose, in an aqueous gel with 1 g/L of pseudomonas syringae. Equal weight samples of this gel and three comparisons were tested. Sample 1 is a gel product called "Artic Ice" a reusable gel ice pack. Sample 2 is Yeti® Ice the refrigerant gel in the Yeti brand ice packs. Sample 3 is the gel from Blue Ice® reusable ice packs sold by Rubbermaid Incorporated.

Each sample was placed in identical containers with a thermocouple probe inserted therein. Each probe was connected to a data logger equipped to monitor temperature over time during the freezing and then the melting of the samples. FIG. 3 is a graph of the freeze data of the samples and FIG. 4 is the melt data of the samples. The temperature range on FIG. 3 is 0 to −10° C. to better illustrate the freeze portion of the data. All samples behaved very similar from room temperature to 0° C. A summary of important times is set forth in Table 2 below.

TABLE 2

| Samples | Time to Reach Freeze Temp (−10° C.) (min) | Time to Reach Thaw Temp (5° C.) (min) | Time to Reach (10° C.) (min) |
|---|---|---|---|
| Comparative Sample 1 - Artic Ice | 520 | 135 | 155 |
| Comparative Sample 2 - Yeti ® Ice | 525 | 115 | 160 |
| Comparative Sample 3 - Blue Ice ® | 525 | 195 | 260 |
| Exp. 1 (1% wt/wt cellulose) | 475 | 285 | 305 |

As shown by the data, the experimental cooling gel froze faster than sample 1, by 45 minutes and lasted longer—taking an additional 150 minutes to reach the thaw temperature of 5° C. As such, the Experimental cooling gel stays cold for more than double the time of Comparative Sample 1. The Experimental cooling gel has improved performance over Comparative Sample 1, especially when reused, since the reset time (time required to freeze) is less. The freezing phase change (liquid to solid) is a key aspect of the efficacy an ice pack. The quickness of freezing directly relates to how fast the product can be reused after it has thawed.

As shown by the data, the experimental cooling gel froze faster than Comparative Sample 2 by 50 minutes and lasted longer—taking an additional 145 minutes to reach the thaw temperature of 5° C. As such, the Experimental cooling gel stays cold for nearly 2.5 times longer than Comparative Sample 2. The Experimental cooling gel has improved performance over Comparative Sample 2, especially when reused, since the reset time (time required to freeze) is considerably less.

The results for Comparative Sample 3 are similar to the other samples. The Experimental cooling gel froze 50 minutes faster and held to 5° C. for 45 minutes longer than Comparative Sample 3. The Experimental cooling gel has improved performance over Comparative Sample 3, especially when reused, since the reset time (time required to freeze) is considerably less.

The enthalpy and free temperature were also measured for the Comparative Samples and the Experimental cooling gel to emphasize the differences and performance attributes. The data was collected by Differential Scanning calorimetry analysis. As shown in Table 3, the Experimental cooling gel out performs the enthalpy of all the Comparative Samples. The Experimental cooling gel has an enthalpy of 321 J/g, which is 24 J/g higher than Comparative Sample 1, 90 J/g higher than Comparative Example 2, and 15 J/g higher than Comparative Example 3.

TABLE 3

| Samples | ΔH | Freeze Temp |
|---|---|---|
| Comparative Sample 1 - Artic Ice | 297 j/g | −12° C. |
| Comparative Sample 2 - Yeti ® Ice | 231 j/g | −15° C. |
| Comparative Sample 3 - Blue Ice ® | 306 j/g | −9.8° C. |
| Exp. 1 (1% wt/wt cellulose) | 321 j/g | −6° C. |

The enthalpy directly equates to how much energy can be stored and released by the gel or ice pack. As such, the higher enthalpy of the Experimental cooling gel means that the cooling gel can stay colder longer than each of the Comparative Samples.

The freeze temperature or freezing point is also significantly higher than the Comparative Samples, which means the Experimental cooling gel reaches its freezing point first and a quicker recharge time.

Having described the invention in detail and by reference to specific embodiments and examples, it will be apparent that numerous modifications and variations are possible without departing from the spirit of the invention as defined by the following claims.

What is claimed is:

1. A thermal cooling gel comprising:

an aqueous gel comprising 1% to 10% wt/wt of cellulose;

0.5 g/L to 2 g/L of the aqueous gel comprises an ice nucleating protein; and a biocide;

wherein the enthalpy of the thermal cooling gel is in a range of 250 J/g to 330 J/g.

2. The thermal cooling gel of claim 1, wherein the cellulose is selected from the group comprising sodium carboxymethylcellulose, hydroxypropyl cellulose, methylcellulose, methyl hydroxyethyl cellulose, methyl hydroxypropyl cellulose, hydroxyethyl cellulose, carboxymethyl methylcellulose, cellulose ethers, mixed cellulose ethers, and combinations thereof.

3. The thermal cooling gel of claim 2, wherein the cellulose comprises methylcellulose.

4. The thermal cooling gel of claim 2, wherein the cellulose comprises methyl cellulose and methyl hydroxyethyl cellulose.

5. The thermal cooling gel of claim 2, wherein the cellulose comprises methyl cellulose, methyl hydroxyethyl cellulose, and methyl hydroxypropyl cellulose.

6. The thermal cooling gel of claim 1, wherein the aqueous gel comprises 1% to 5% wt/wt cellulose and has an enthalpy in a range of 300 J/g to 330 J/g.

7. The thermal cooling gel of claim 6, wherein the aqueous gel has a viscosity of 25 cps to 7,000 cps.

8. The thermal cooling gel of claim 1, wherein the aqueous gel comprises 5% to 10% wt/wt cellulose, and has an enthalpy in a range of 250 J/g to 300 J/g.

9. The thermal cooling gel of claim 6, wherein the aqueous gel has a viscosity of 7,000 cps to 65,000 cps.

10. The thermal cooling gel of claim 1, wherein the ice nucleating protein is selected from the group consisting of pseudomonas syringae, pseudomonas fluorescens, Erwinaia herbicola, and combinations thereof.

11. The thermal cooling gel of claim 1, wherein the biocide is selected from the group consisting of silver nanoparticles, an herb extract of thyme, and combinations thereof.

12. The thermal cooling gel of claim 1, wherein the biocide is 0.001% to 1% wt/wt of the aqueous gel.

13. A cold pack comprising:
a container;
a thermal cooling gel enclosed within the container, wherein the thermal cooling gel comprises:
an aqueous gel comprising 1% to 10% wt/wt of cellulose;
0.5 g/L to 2 g/L of the aqueous gel comprises an ice nucleating protein; and
a biocide;
wherein the enthalpy of the thermal cooling gel is in the range of 250 J/g to 330 J/g.

14. The cold pack of claim 13, wherein the container permanently encloses the thermal cooling gel.

15. The cold pack of claim 13, wherein the container is a rigid container that retains a preselected shape and configuration.

16. The cold pack of claim 13, wherein the container is a flexible container that is conformable to a surface against which the flexible container is seated.

17. The thermal cooling gel of claim 13, wherein the cellulose is selected from the group comprising sodium carboxymethylcellulose, hydroxypropyl cellulose, methylcellulose, methyl hydroxyethyl cellulose, methyl hydroxypropyl cellulose, hydroxyethyl cellulose, carboxymethyl methylcellulose, cellulose ethers, mixed cellulose ethers, and combinations thereof.

18. The thermal cooling gel of claim 13, wherein the aqueous gel comprises 1% to 5% wt/wt cellulose and has an enthalpy in a range of 300 J/g to 330 J/g and has a viscosity of 25 cps to 7,000 cps.

19. The thermal cooling gel of claim 13, wherein the aqueous gel comprises 5% to 10% wt/wt cellulose and has an enthalpy in a range of 250 J/g to 300 J/g and has a viscosity of 7,000 cps to 65,000 cps.

20. The thermal cooling gel of claim 13, wherein the ice nucleating protein is selected from the group consisting of pseudomonas syringae, pseudomonas fluorescens, Erwinaia herbicola, and combinations thereof.

21. The thermal cooling gel of claim 13, wherein the biocide is selected from the group consisting of silver nanoparticles, an herb extract of thyme, and combinations thereof.

22. The thermal cooling gel of claim 13, wherein the biocide is 0.001% to 1% wt/wt of the aqueous gel.

* * * * *